United States Patent [19]

Burke

[11] Patent Number: 5,485,042
[45] Date of Patent: Jan. 16, 1996

[54] MOTOR DRIVE UNIT WITH TORQUE CONTROL CIRCUIT

[75] Inventor: Phillip C. Burke, Temecula, Calif.

[73] Assignee: Devices for Vascular Intervention, Inc., Redwood City, Calif.

[21] Appl. No.: 319,200

[22] Filed: Oct. 6, 1994

Related U.S. Application Data

[62] Division of Ser. No. 982,814, Nov. 30, 1992, Pat. No. 5,372,602.

[51] Int. Cl.⁶ .......................... H02K 11/00; H02K 7/14; H02P 7/06
[52] U.S. Cl. .......................... 310/47; 310/68 R; 318/459
[58] Field of Search .......................... 310/47, 50, 68 R; 318/138, 254, 432, 439; 361/29; 388/921, 937

[56] References Cited

U.S. PATENT DOCUMENTS

| Re. 33,569 | 4/1991 | Gifford, III et al. | 606/159 |
|---|---|---|---|
| 3,402,337 | 9/1968 | Malmborg et al. | 318/254 |
| 3,573,580 | 4/1971 | Shinozaki | 318/778 |
| 3,721,832 | 3/1973 | Lee | 361/29 |
| 3,742,370 | 6/1973 | Hansen | 318/778 |
| 4,455,513 | 6/1984 | Fulton et al. | 318/138 |
| 4,484,114 | 11/1984 | Ebbs | 318/138 |
| 4,638,226 | 1/1987 | Daminano et al. | 310/331 |
| 4,679,557 | 7/1987 | Opie et al. | 606/180 |
| 4,705,038 | 11/1987 | Sjostrom et al. | 606/180 |
| 4,747,821 | 5/1988 | Kensey et al. | 604/22 |
| 4,763,347 | 8/1988 | Erdman | 310/254 |
| 4,771,774 | 9/1988 | Simpson et al. | 128/305 |
| 4,847,541 | 7/1989 | Krieger | 318/468 |
| 4,867,155 | 9/1989 | Isaacson | 606/180 |
| 4,936,845 | 6/1990 | Stevens | 606/180 |
| 4,979,951 | 12/1990 | Simpson | 606/159 |
| 4,995,877 | 2/1991 | Ams et al. | 606/180 |
| 5,002,553 | 3/1991 | Shiber | 604/22 |
| 5,071,425 | 12/1991 | Gifford, III et al. | 606/159 |
| 5,100,425 | 3/1992 | Fischell et al. | 604/22 |
| 5,181,920 | 1/1993 | Mueller et al. | 606/180 |

*Primary Examiner*—Clayton E. LaBalle
*Attorney, Agent, or Firm*—Townsend and Townsend and Crew

[57] ABSTRACT

The invention provides a motor drive unit for use in conjunction with an atherectomy device which limits the torque exerted on a drive cable for rotating a cutting blade in the device. In a preferred embodiment, a motor drive unit includes a motor having a shaft coupled to the drive cable for rotating the cutting blade, a power supply coupled to the motor and a switch for selectively connecting the power supply to the motor. A torque control circuit connected to the power supply and the motor controls the torque exerted by the motor when the switch is closed, whereby the current to the motor is continuously increased from zero to a start-up level, the start-up level being the minimum current sufficient to turn the cutting blade. Usually, the torque control circuit will include a resistor and a capacitor connected to a power supply in parallel with the motor, wherein a gradually decreasing portion of current from the battery is diverted through the RC circuit to charge the capacitor such that the current to the motor is at the start-up level when the capacitor is charged. The motor drive unit further includes a power MOSFET for discharging the capacitor when the switch is opened to reset the circuit.

16 Claims, 3 Drawing Sheets

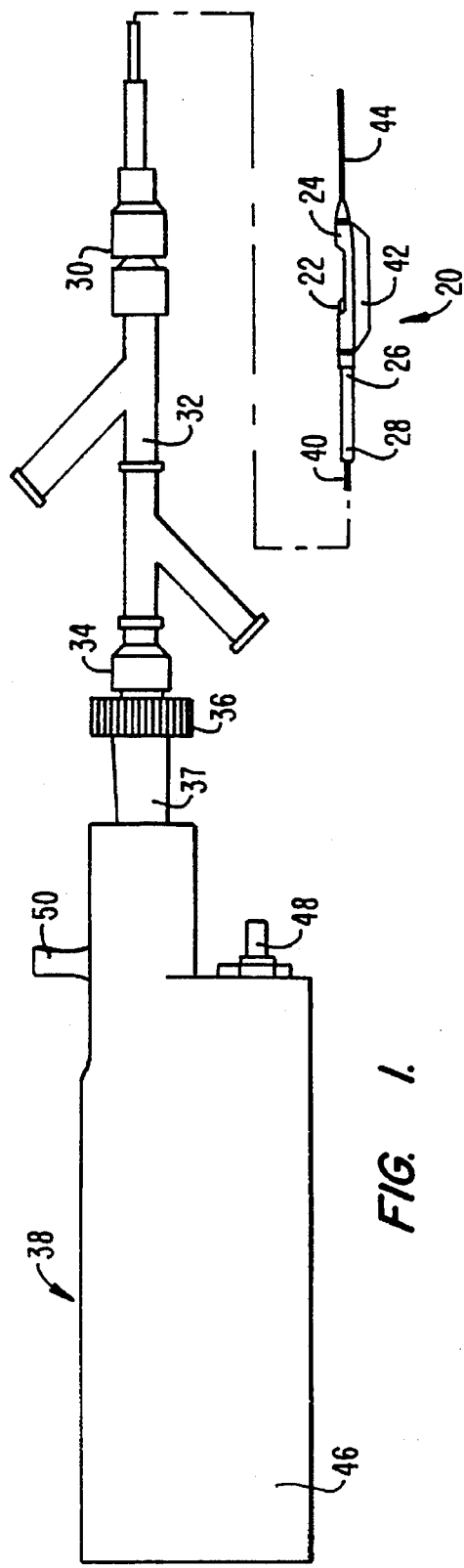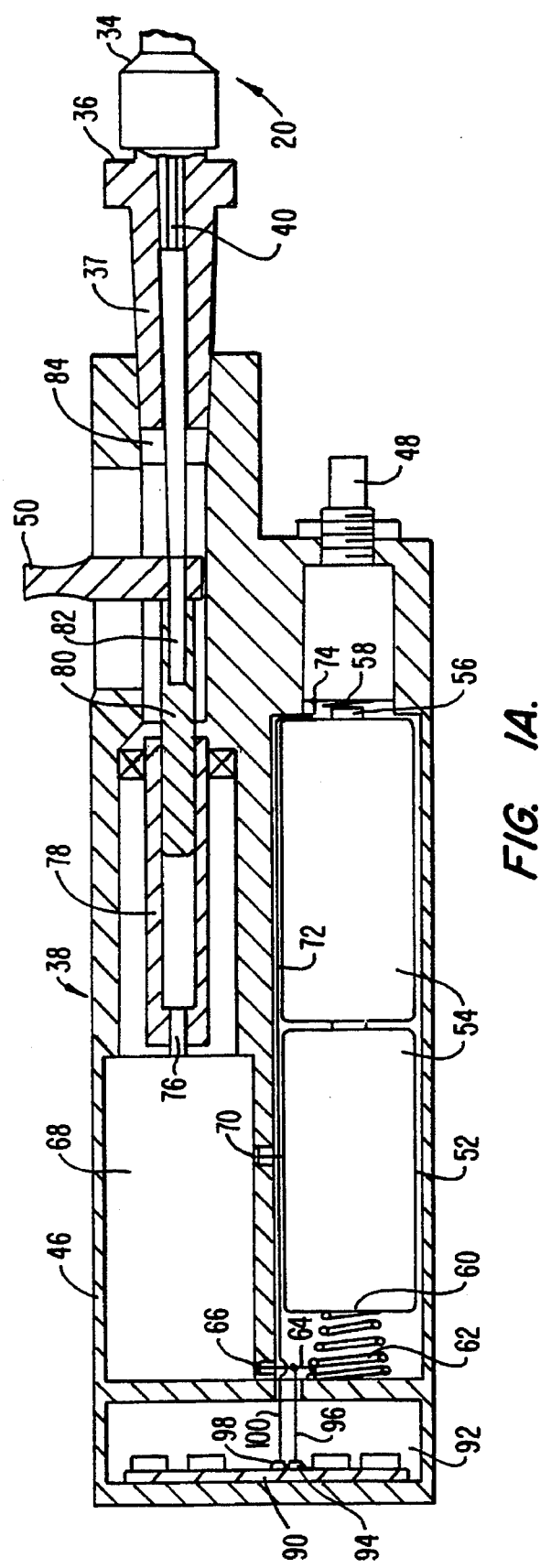
FIG. 1.
FIG. 1A.

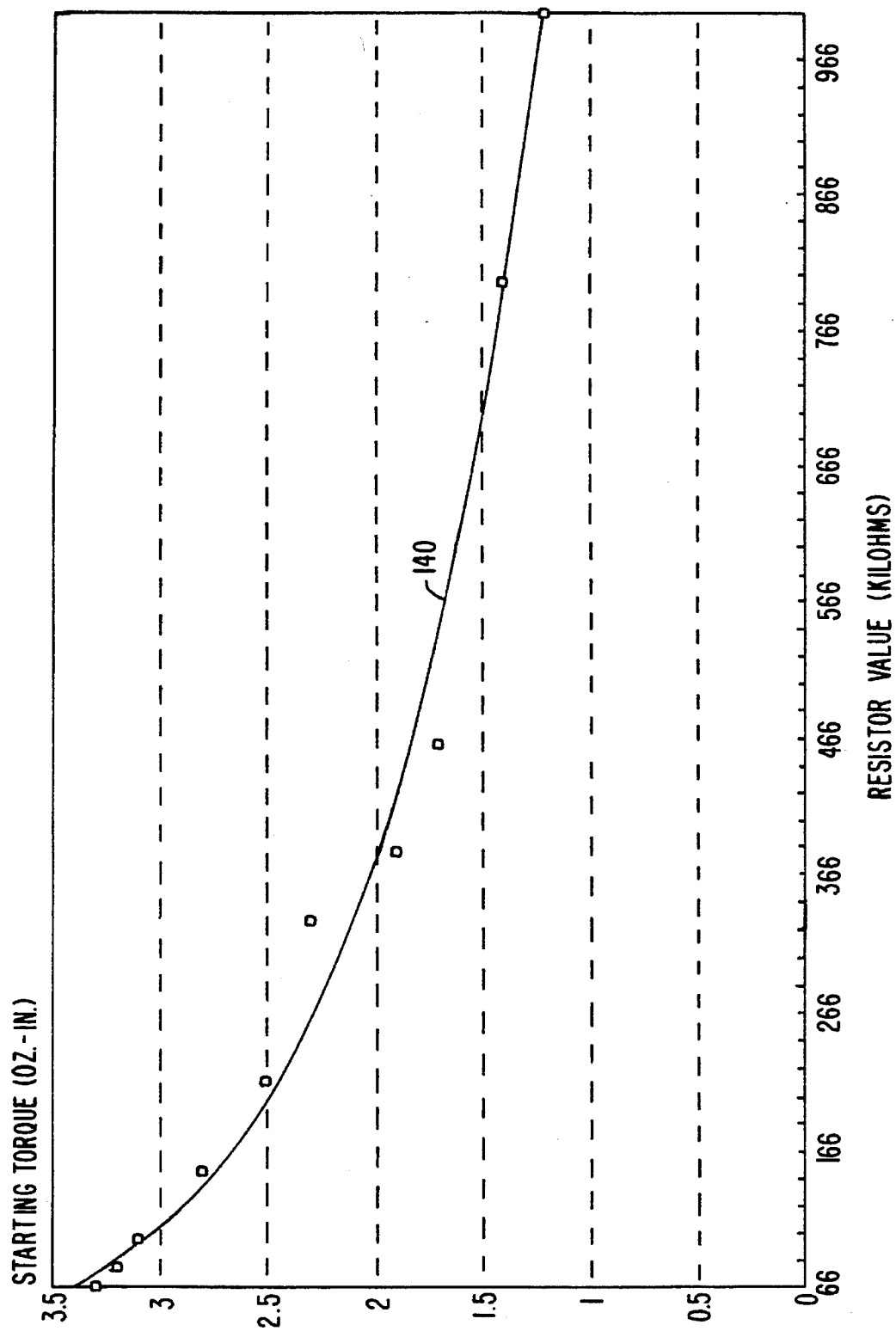

MOTOR DRIVE UNIT WITH TORQUE CONTROL CIRCUIT

This is a Division of application Ser. No. 07/982,814, filed Nov. 30, 1992, now U.S. Pat. No. 5,372,602.

BACKGROUND OF THE INVENTION

FIELD OF THE INVENTION

The present invention relates generally to surgical instruments, and more particularly to a motor drive unit for use in conjunction with an atherectomy device.

Atherectomy devices have been developed for the treatment of coronary artery disease by cutting diseased tissue along the wall of an artery. To accomplish this, an elongated catheter shaft having a cutting blade at its distal end is positioned in the artery near the diseased region. The cutting blade is attached to a drive cable which extends through the shaft from the proximal end, where it is coupled to a motor drive unit. The motor drive unit applies torque to the drive cable in order to rotate the cutting blade, thereby severing diseased tissue.

U.S. Pat. No. 4,771,774 to Simpson, et al., issued Sep. 20, 1988, the full disclosure of which is incorporated herein by reference, describes a motor drive unit for use in connection with an atherectomy device. The motor drive unit includes a case having a size and shape appropriate for being hand held. A motor is mounted in the case, along with a power supply, usually comprising one or more batteries, providing power to the motor. A switch is mounted in the case and is accessible for finger operation by the user. The motor drive unit connects to the proximal end of the shaft of the atherectomy device. Upon activation of the switch, the motor applies a torque to the proximal end of the drive cable, thereby rotating the cutting blade.

Although such atherectomy devices are generally effective, the motor drive unit used with such devices has suffered from certain problems. In particular, upon start-up, the motor drive unit has been found to apply a torque to the drive cable of the device of such magnitude that the cable fails. Typically, this occurs when the cutting blade and/or the drive cable are bound due to engagement of the blade or a tortuous configuration of the shaft. In such a situation, when the switch is turned on, the motor instantaneously applies a torque pulse to the drive cable which exceeds the torsional strength limit of the cable.

Therefore, an improved motor drive unit for use with an atherectomy device is desired which would limit the initial torque applied by the motor to the drive cable upon start-up to a level lower than the torsional strength limit of the cable. Preferably, the motor drive unit should undergo a ramp-up from a power-off state to a power level sufficient to turn the blade and cable, providing a smooth and continuous increase in power delivered from the power supply to the motor. Further, the performance of the motor drive unit should not be affected once the blade has begun to turn.

SUMMARY OF THE INVENTION

The present invention provides a motor drive unit (MDU) for use with an atherectomy device of the type having a rotatable cutting blade driven by a drive cable, wherein the torque applied to the drive cable by the MDU is limited so as not to exceed the torsion strength limit of the drive cable. The problems associated with prior motor drive units in severing the drive cable upon start-up are eliminated. At the same time, after start-up, the MDU performs substantially identically to MDUs without torque limiting capabilities.

In a preferred embodiment, the motor drive unit of the present invention comprises a motor having a shaft coupled to the drive cable of the atherectomy device for rotating the cutting blade, a power supply coupled to the motor, a switch for selectively connecting the power supply to the motor and a torque control circuit connected to the power supply and the motor for controlling the torque exerted by the motor when the switch is closed. The torque control circuit causes the current conducted to the motor to be continuously increased from zero to a start-up level, wherein the start-up level is the minimum current sufficient to turn the cutting blade. By ramping-up the current gradually and continuously from the zero to the start-up level, the torque control circuit eliminates the torque pulse exerted by known MDUs upon the drive cable when, for example, the cutting blade and/or the drive cable are bound or otherwise restricted in motion.

In a preferred aspect, the torque control circuit includes an RC circuit connected to the power supply in parallel with the motor. The RC circuit will include a capacitor and a resistor, and, upon start-up, a gradually decreasing portion of current from the battery will be diverted through the RC circuit to charge the capacitor, such that the current to the motor is at the start-up level when the capacitor is fully charged.

Usually, the motor drive unit will further include means for discharging the capacitor when the switch is opened. In a preferred embodiment, the means for discharging will comprise a transistor having a gate, source and drain electrode, wherein the gate electrode is connected to the RC circuit, the source electrode is connected to the power supply and the drain electrode is connected to the motor. Usually, the transistor will be a power MOSFET.

The motor drive unit exerts a start-up torque on the drive cable when the current to the motor is at the start-up level which is proportional to the resistance of the resistor in the RC circuit. In a preferred embodiment, the resistor will be chosen so that the start-up torque is less than 3.0 oz.-in.

The invention further provides a method for removing plaque from an interior wall of a vessel, which will usually be an artery. The method includes positioning a catheter in the vessel, the catheter having a cutting blade at its distal end, a motor at its proximal end and a drive cable coupled between the motor and the cutting blade, the catheter being positioned such that the cutting blade is disposed near the plaque. Current is then supplied from a power supply to the motor so as to apply torque to a proximal end of the drive cable. The current to the motor is controlled such that the current continuously rises from zero to a start-up level, the start-up level being the minimal current sufficient to turn the cutting blade. With the cutting blade turning, the plaque is engaged with the blade.

In a preferred aspect of the method of the invention, the torque is controlled by a torque control circuit connected to the power supply in the motor. Usually the torque control circuit will comprise, as described above, an RC circuit connected to the power supply in parallel with the motor, such that upon start-up, a gradually decreasing portion of current from the power supply is diverted around the motor through the RC circuit to charge the capacitor. The current to the motor will be the start-up level when the capacitor is charged. As described above, the torque control circuit will preferably include means for discharging the capacitor when the power supply is disconnected, which will usually comprise a power MOSFET.

In a further preferred embodiment, the torque control circuit will also include a diode having a first terminal connected to the RC circuit between the resistor and the capacitor, and a second terminal connected between the motor and the switch. The diode serves to draw power off of the motor when the switch is opened by diverting current around the resistor in the RC circuit.

BRIEF DESCRIPTION OF THE DRAWINGS

FIG. 1 is a side elevational view of a motor drive unit constructed in accordance with the principles of the present invention connected to an atherectomy device.

FIG. 1A is a side cross-sectional view of the motor drive unit of FIG. 1.

FIG. 3 is a graph of starting torque as a function of the value of the resistor of the torque control circuit of FIG. 2.

DESCRIPTION OF SPECIFIC EMBODIMENTS

Figure 2:
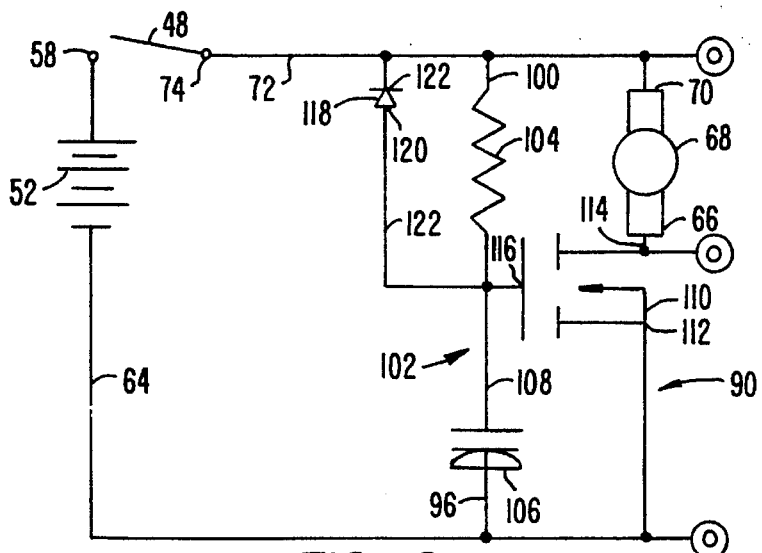
FIG. 2 is a circuit diagram of the torque control circuit of the motor drive unit of FIG. 1

FIGS. 1 and 1A illustrate a motor drive unit for use with an atherectomy device according to the principles of the present invention. It should be understood that the physical configuration of the motor drive unit is not critical, and the invention as claimed herein may be embodied in motor drive units of various shapes, sizes and structures. Referring to FIG. 1, the atherectomy device 20 will include cutting means at its distal end including a rotatable cutting blade 22 slidably disposed in a housing 24. Housing 24 will be connected to the distal end 26 of a flexible shaft 28, which connects at its proximal end 30 to an adaptor 32. Adaptor 32 connects at its proximal end 34 to motor drive unit 38 by means of a tapered fitting 37 adapted to be received in case 46, as described more fully below. Shaft 28 will have a longitudinal passage in which is disposed a rotatable drive cable 40 to which cutting blade 22 is attached. Distal housing 24 may further include an expandable balloon 42 disposed on a side of housing 24 opposite cutting blade 22. Shaft 28 and housing 24 will also provide a passage for a movable guide wire 44.

Motor drive unit 38 will include a case 46, which usually will be configured to be held by a single hand. A switch 48 is mounted to case 46, preferably in a position to be actuated by the finger of the user. A finger-operated slide member 50 may further be provided for advancing cutting blade 22 in the axial direction.

Referring now to FIG. 1A, MDU 38 includes within case 46 a power supply 52, which usually will comprise one or more batteries 54. Batteries 54 are electrically connected at end 56 to a contact 58 of switch 48. At end 60, batteries 54 are electrically coupled to a spring contact 62. Spring contact 62 is connected by conductor 64 to a first terminal 66 of drive motor 68. A second terminal 70 of drive motor 68 is connected by means of conductor 72 to a second contact 74 of switch 48. Motor 68 is thereby switchably connected to power supply 52, for driving the cutting blade 22 of atherectomy device 20.

Drive motor 68 has a drive shaft 76 coupled to a shaft extension 78, which engages a drive spline 80 coupled to a connecting shaft 82. The proximal end of drive cable 40 is fastened to connecting shaft 82 by crimping or other known means. Tapered fitting 37 of atherectomy device 20 is received in tapered bore 84 in case 46 to effect a tight connection between atherectomy device 20 and MDU 38. Further details of the mechanical aspects of MDU 38 and atherectomy device 20 are described in U.S. Pat. No. 4,771,774, which has been incorporated herein by reference. It will be understood that the physical configuration of the MDU 38 and atherectomy device 20 are not critical to the present invention, which is adaptable to any motor drive unit usable in conjunction with an atherectomy device which has a rotating cutting blade driven by a flexible drive shaft. The invention may find further application in a variety of power tools for both surgical and non-surgical purposes, wherein the torque exerted by a drive motor upon a shaft would be desirably be limited so as to eliminate excessive torsional stress on the shaft upon startup.

The torque limiting features of the present invention are accomplished, in a preferred embodiment, by a torque control circuit 90, which may be mounted at any convenient location within case 46, shown in the figures in a proximal compartment 92. Torque control circuit 90 has a first terminal 94 connected by a conductor 96 to conductor 64, providing electrical connection to power supply 52. A second terminal 98 is connected via conductor 100 to conductor 72 from second contact 74 of switch 48. Thus, torque control circuit 90 is connected to power supply 52 in parallel with drive motor 68.

Referring now to FIG. 2, torque control circuit 90 includes an RC circuit 102 having a resistor 104 and a capacitor 106 connected in series. A first terminal of capacitor 106 is connected by conductor 96 to conductor 64 and power supply 52. A second terminal of capacitor 106 is connected via conductor 108 to a first end of resistor 104, while a second end of resistor 104 is connected through conductors 100, 72 to terminal 74 of switch 48.

In a specific embodiment, torque control circuit 90 will further include means for resetting the circuit by discharging capacitor 106 when switch 48 is opened. In a preferred embodiment, the resetting means will comprise a power MOSFET 110 connected to RC circuit 102 and drive motor 68. MOSFET 110 will include a source electrode 112 connected to power supply 52, drain electrode 114 connected to terminal 66 of drive motor 68 and gate electrode 116 connected to conductor 108 of RC circuit 102.

In a further aspect of the torque control circuit of the present invention, a diode 118 will be provided to draw power from the motor 68 when switch 48 is opened. Diode 118 will have first terminal 120 connected by a conductor 122 to conductor 108 between capacitor 106 and resistor 104. A second terminal 122 of diode 118 will be connected to conductor 72 and switch 48.

In an exemplary embodiment, for a 6-volt DC power supply 52 and 2-watt DC motor, capacitor 106 will be 0.68 microfarads, resistor 104 will be 330K ohms, power MOSFET 110 will be an IRF Z20, and diode 118 will be an 1N914 or 1N4148.

Preferably, the torque control circuit 90 will comprise a printed circuit board having through-hole or surface-mount components mounted thereon. The torque control circuit may alternatively be embodied in an integrated circuit package.

In operation, torque control circuit 90 serves to ramp-up the current to motor 68 upon start-up from zero to a start-up level, the start-up level being the minimum current required to rotate drive shaft 40 and cutting blade 22. When switch 48 is closed, current flows through conductor 64 to RC circuit 102 as well as motor 68. Initially, most of the current from power supply 52 will be conducted to RC circuit 102 to charge capacitor 106. As capacitor 106 charges, a decreasing amount of current will be conducted to it, with an increasing portion of current being conducted to motor 68. When capacitor 106 is fully charged, substantially all the current will flow through motor 68, so that RC circuit 102 is invisible in the operation of the motor drive unit. Preferably, capacitor 106 will become fully charged, and the current to motor 68 will be ramped-up to the start-up level, over a period of approximately 0.6 second. This ramp-up period may be varied by changing the resistance of resistor 104 in RC circuit 102.

Figure 4:
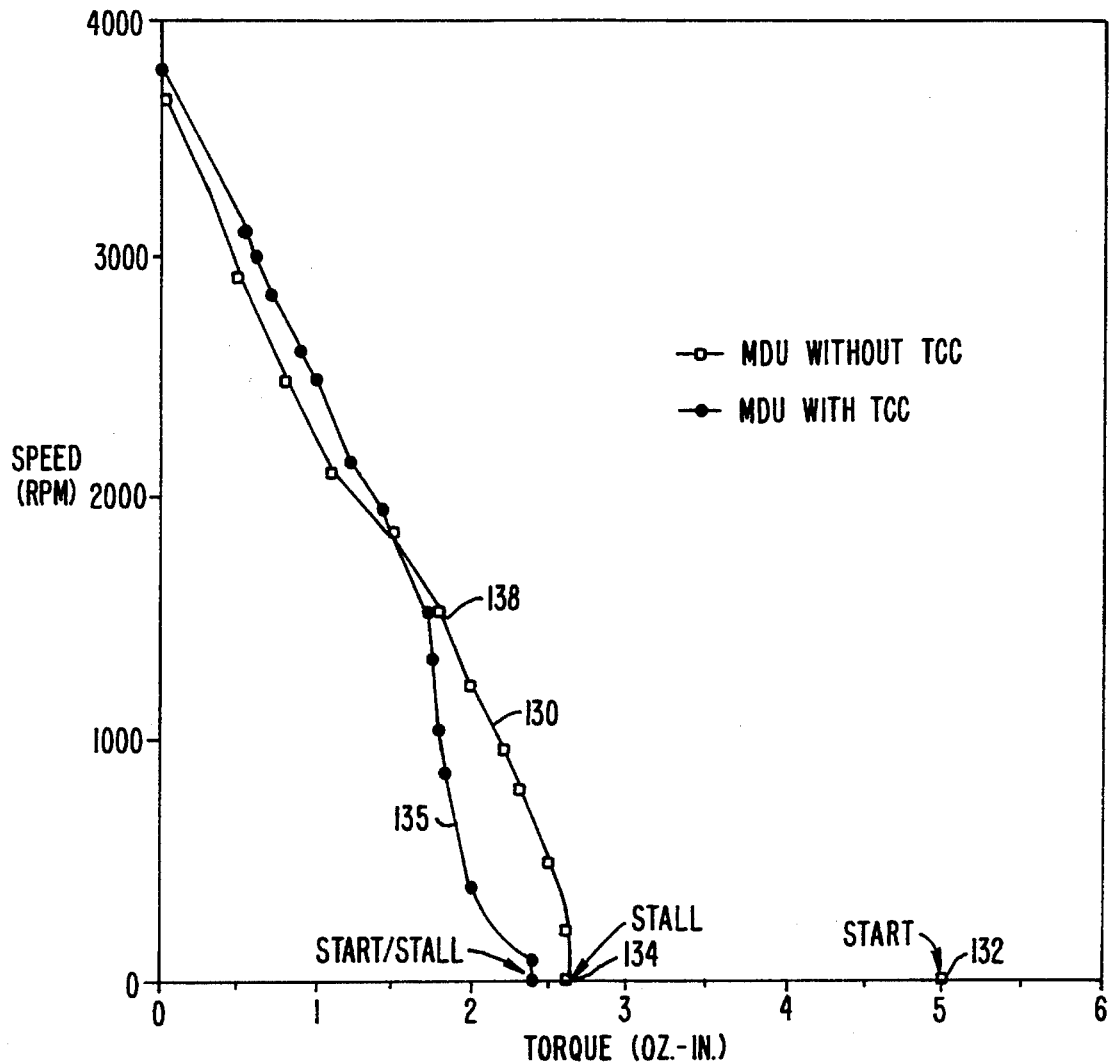
FIG. 4 is a graph of torque exerted by the motor on the drive cable of the atherectomy device as a function of speed of the torque control circuit of FIG. 2.

In FIG. 4, the torque exerted by the MDU on drive shaft 40 is plotted as a function of motor speed. In the MDU without torque control circuit 90 (curve 130), it may be seen that, upon start-up, an initial torque pulse is exhibited which is nearly twice the maximum torque on the shaft during rotation of cutting blade 22. In the example plotted in the figure, torque pulse 132 has a magnitude of approximately 5.0 oz.-in., while the torque exerted during rotation of the shaft has a maximum at about 2.7 oz.-in. at the point of stall 134. It may be further seen that the torque decreases to approximately zero as the speed of the motor increases from zero to about 3800 rpm.

In contrast, the MDU having a torque control circuit 92, represented in curve 135, exhibits a start-up torque approximately equal to the torque at stall, around 2.4 oz.-in. at point 136. The torque exerted by the motor on drive shaft 40 is slightly less than that of the MDU without the torque control circuit up to a point 138, approximately 1600 rpm, from which the performance of the MDU with the torque control circuit was substantially identical to that without the torque control circuit. Thus, in the example of FIG. 4, where the maximum torsional strength limit of drive cable 40 is between about 2.4 oz.-in. and about 5.0 oz.-in., the motor drive unit without torque control will cause the drive cable to fail, while the motor drive unit of the present invention using a torque control circuit will provide a soft start of the motor which eliminates cable failure.

Referring to FIG. 3, it may be seen that the starting torque exerted by drive motor 68 on drive cable 40 at start-up may be selected by appropriate selection of resistor 104 in RC circuit 102. Curve 140 illustrates that the starting torque varies inversely with the resistance value of resistor 104, permitting, in an exemplary embodiment, selection of starting torque in a range between about 1.2 and 3.5 oz.-in. using resistors with resistances between 0 and 1000 kΩ.

Torque control circuit 90 further provides, as described above, means for resetting the circuit when switch 48 is opened. In a preferred embodiment, this reset function is performed by power MOSFET 110 connected to motor 68 and RC circuit 102. When switch 48 is opened, power MOSFET 110 acts as a switch to drain power from capacitor 106, thereby returning capacitor 106 to a discharged state. The torque control circuit 90 is thereby ready for the next start-up of MDU 38.

Upon opening switch 48, diode 118 serves to draw power off of motor 68 by providing a conductive path around resistor 104.

In the method of the present invention, the atherectomy device 20 is positioned in a vessel, which usually will comprise an artery. Cutting blade 22 at the distal end of the catheter will be positioned near a treatment site in the vessel, typically a diseased region of an artery, commonly having plaque or stenosis on the artery wall. Current is then supplied to the motor 68 by actuating switch 48, so that the motor applies torque to the proximal end of drive cable 40. Torque control circuit 90 controls the current flowing to motor 68 such that the current continuously increases from zero to a start-up level, the start-up level being the minimum level sufficient to turn cutting blade 22. The rotating cutting blade is then positioned to engage the plaque. Preferably, the start-up torque will be proportional to the resistance of resistor 104 in the RC circuit 102, which will be selected so that the start-up torque is less than 3.0 oz.-in.

When the switch 48 is switched off, disconnecting motor 68 from power supply 52, power MOSFET 110 will discharge capacitor 106 so as to reset the torque control circuit to be operable the next time switch 48 is closed. In addition, when switch 48 is opened, diode 118 will draw power off of motor 68.

Using the motor drive unit with torque control circuit according to the present invention, even where drive cable 40 or cutting blade 22 are bound by friction or interference, the motor drive unit may be started from a poweroff state without risk of severing drive cable 40 as frequently occurred in previous motor drive units. At the same time, after an initial start-up period, the motor drive unit performs substantially unaffected by the torque control circuit. Moreover, upon turning power off in the motor drive unit, the torque control circuit automatically resets in preparation for repeated uses. Moreover, the compact size of the torque control circuit permit it to be easily integrated into motor drive units of various configurations without major design changes or expense.

While the above is a complete description of the preferred embodiments of the invention, various alternatives, modifications, and equivalents may be used. Therefore, the above description should not be taken as limiting the scope of the invention which is defined by the appended claims.

What is claimed

1. A motor drive unit for use in conjunction with an atherectomy device, the atherectomy device having an elongated flexible body, a cutting blade near a distal end of the body, and a drive cable aligned with the body and coupled to the cutting blade, the motor drive unit comprising:

a direct current motor having a shaft coupled to the drive cable for rotating the cutting blade;

a power supply coupled to the motor;

a switch for selectively connecting the power supply to the motor; and a torque control circuit connected to the power supply in parallel with the motor for controlling torque exerted by the motor when the switch is closed whereby direct current supplied by the power supply is divided between the torque control circuit and the motor, with the direct current supplied to the motor being continuously increased from zero to a start-up level, the start-up level being the minimum current sufficient to turn the cutting blade.

2. A motor drive unit as in claim 1 wherein the torque control circuit includes an RC circuit connected to the power supply in parallel with the motor, the RC circuit having a capacitor and a resistor, wherein a gradually decreasing portion of direct current from the power supply is diverted through the RC circuit to charge the capacitor, the direct current to the motor being the start-up level when the capacitor is charged.

3. A motor drive unit as in claim 2 wherein the torque control circuit further comprises means for discharging the capacitor when the switch is opened.

4. A motor drive unit as in claim 3 wherein the means for discharging comprises a transistor having gate, source and drain electrodes, the gate electrode being connected to the RC circuit, the source electrode being connected to the power supply and the drain electrode being connected to the motor.

5. A motor drive unit as in claim 4 wherein the transistor is a power MOSFET.

6. A motor drive unit as in claim 2 wherein a start-up torque is exerted on the drive cable at the start-up current level, the start-up torque being proportional to the resistance of the resistor.

7. A motor drive unit as in claim 6 wherein the start-up torque is less than 3.0 ounce inches.

8. A motor drive unit for use in conjunction with an atherectomy device, the atherectomy device having an elongated flexible body, a cutting blade near a distal end of the body, and a drive cable aligned with the body and coupled to the cutting blade, the motor drive unit comprising:

a direct current motor having a shaft coupled to the drive cable for rotating the cutting blade;

a power supply connected to the motor;

a switch for selectively connecting the power supply to the motor; and an RC circuit connected to the power supply in parallel with the motor, the RC circuit having a capacitor and a resistor, wherein upon closing the switch, the direct current is divided between the RC circuit and the motor, with a gradually decreasing portion of direct current from the power supply being diverted around the motor through the RC circuit to charge the capacitor such that direct current to the motor continuously increases from zero to a start-up level, the start-up level being the minimum direct current sufficient to turn the cutting blade.

9. A motor drive unit as in claim 8 wherein the torque control circuit further comprises means for discharging the capacitor when the switch is opened.

10. A motor drive unit as in claim 9 wherein the means for discharging comprises a transistor having gate, source and drain electrodes, the gate electrode being connected to the RC circuit, the source electrode being connected to a first terminal of the power supply and the drain electrode being connected to the motor.

11. A motor drive unit as in claim 10 wherein the transistor is a power MOSFET.

12. A motor drive unit as in claim 10 wherein the torque control circuit further comprises a diode, a first terminal of the diode being connected to the RC circuit between the resistor and the capacitor and a second terminal of the diode being connected between the motor and the switch.

13. A motor drive unit as in claim 8 wherein a start-up torque is exerted on the drive cable at the start-up current level, the start-up torque being proportional to the resistance of the resistor.

14. A motor drive unit as in claim 13 wherein the start-up torque is less than 3.0 oz. inches 15. A motor drive unit for use in conjunction with an atherectomy device, the atherectomy device having an elongated flexible body, a cutting blade near a distal end of the body, and a drive cable aligned with the body and coupled to the cutting blade, the motor drive unit comprising:

a motor having a shaft coupled to the drive cable for rotating the cutting blade;

a power supply coupled to the motor;

a switch for selectively connecting the power supply to the motor; and a torque control circuit connected to the power supply and the motor for controlling torque exerted by the motor when the switch is closed whereby current to the motor is continuously increased from zero to a start-up level, the start-up level being the minimum current sufficient to turn the cutting blade, wherein the torque control circuit includes an RC circuit connected to the power supply in parallel with the motor, the RC circuit having a capacitor and a resistor, wherein a gradually decreasing portion of current from the power supply is diverted through the RC circuit to charge the capacitor, the current to the motor being the start-up level when the capacitor is charged, wherein the torque control circuit further comprises means for discharging the capacitor when the switch is opened, and wherein the means for discharging comprises a transistor having gate, source and drain electrodes, the gate electrode being connected to the RC circuit, the source electrode being connected to the power supply and the drain electrode being connected to the motor.

16. A motor drive unit for use in conjunction with an atherectomy device, the atherectomy device having an elongated flexible body, a cutting blade near a distal end of the body, and a drive cable aligned with the body and coupled to the cutting blade, the motor drive unit comprising:

a motor having a shaft coupled to the drive cable for rotating the cutting blade;

a power supply connected to the motor;

a switch for selectively connecting the power supply to the motor; and an RC circuit connected to the power supply in parallel with the motor, the RC circuit having a capacitor and a resistor, wherein upon closing the switch, a gradually decreasing portion of current from the power supply is diverted around the motor through the RC circuit to charge the capacitor such that current to the motor continuously increases from zero to a start-up level, the start-up level being the minimum current sufficient to turn the cutting blade, wherein the torque control circuit further comprises means for discharging the capacitor when the switch is opened, and wherein the means for discharging comprises a transistor having gate, source and drain electrodes, the gate electrode being connected to the RC circuit, the source electrode being connected to a first terminal of the power supply and the drain electrode being connected to the motor.

* * * * *